(12) United States Patent
Stiernborg

(10) Patent No.: US 7,572,258 B2
(45) Date of Patent: Aug. 11, 2009

(54) MITRE INSTRUMENT, AS AN EXAMPLE FOR HALLUX SURGERY

(76) Inventor: Claes-Olof Stiernborg, Filuftsvagen 8, Lidingo (SE) 181 30

(*) Notice: Subject to any disclaimer, the term of this patent is extended or adjusted under 35 U.S.C. 154(b) by 641 days.

(21) Appl. No.: 10/515,055

(22) PCT Filed: May 23, 2003

(86) PCT No.: PCT/SE03/00841
§ 371 (c)(1),
(2), (4) Date: Jun. 6, 2005

(87) PCT Pub. No.: WO03/099144
PCT Pub. Date: Dec. 4, 2003

(65) Prior Publication Data
US 2005/0228389 A1    Oct. 13, 2005

(30) Foreign Application Priority Data
May 23, 2002  (SE) .................................. 0201547
Feb. 7, 2003  (SE) .................................. 0300315

(51) Int. Cl.
*A61B 17/00* (2006.01)
(52) U.S. Cl. ......................................................... 606/79
(58) Field of Classification Search .................. 606/79, 606/80, 82, 69, 70, 96, 280, 86 R
See application file for complete search history.

(56) References Cited
U.S. PATENT DOCUMENTS

| 4,421,112 | A |   | 12/1983 | Mains et al. |
| 5,306,278 | A | * | 4/1994 | Dahl et al. ...................... 606/96 |
| 5,449,360 | A |   | 9/1995 | Schreiber |
| 5,578,036 | A | * | 11/1996 | Stone et al. .................... 606/69 |
| 5,613,969 | A |   | 3/1997 | Jenkins, Jr. |
| 5,843,085 | A |   | 12/1998 | Graser |
| 5,916,200 | A | * | 6/1999 | Eppley et al. ................ 604/178 |
| 5,961,519 | A | * | 10/1999 | Bruce et al. .................... 606/69 |
| 6,168,600 | B1 | * | 1/2001 | Grace et al. .................... 606/81 |
| 6,179,839 | B1 | * | 1/2001 | Weiss et al. .................... 606/69 |
| 6,206,882 | B1 | * | 3/2001 | Cohen ........................... 606/69 |
| 6,361,538 | B1 | * | 3/2002 | Fenaroli et al. ................ 606/73 |
| 6,500,179 | B1 |   | 12/2002 | Masini |
| 2003/0083663 | A1 | * | 5/2003 | Goldhahn et al. .............. 606/73 |
| 2003/0149433 | A1 | * | 8/2003 | Hehli et al. .................... 606/69 |

FOREIGN PATENT DOCUMENTS
EP    570187 A1    11/1993

* cited by examiner

*Primary Examiner*—Eduardo C Robert
*Assistant Examiner*—Michael J Araj
(74) *Attorney, Agent, or Firm*—Dowell & Dowell, P.C.

(57) ABSTRACT

A mitre instrument for use during surgery when cutting bone in connection with shortening or extension and/or correcting of the angle of the bone. The mitre instrument includes a body (9), in which there is at least one hole for a guide pin (13) for fixation of the instrument and at least two slots or scores (3) for a cutting tool (11). The slots (3) are provided in an oblique form relative each other and in predetermined, fixed angles, which converge in a common origin of coordinates (0), at the same time as the cutting tool (11) is extendable from the lower side of the body (9) at an outlet for a guide pin (13) in origin (0) without the wedge-shaped portions (2) of the body (9) therebetween falling off.

10 Claims, 5 Drawing Sheets

MITRE INSTRUMENT, AS AN EXAMPLE FOR HALLUX SURGERY

BACKGROUND OF THE INVENTION

1. Field of the Invention

The present invention regards a mitre instrument, as an example for hallux surgery and which is intended for use during surgery when cutting bone in connection with shortening or extension and/or correction of the angle of the bone and which instrument comprises a disc shaped body, in which there is at least one hole intended for a guide pin for securing of the instrument and at least two slots or scores for a cutting tool.

2. Brief Description of Related Art

Today there is a large number of different methods described on how to operate for example hallux valgus and rigidus. Nearly every method has an own name after the surgeon/orthopedist that describes the operation procedure, for example McBride, Keller, Lapidus, Scarf, Reverdin, Akin, Waterman, Youngswick, Mitchell, Turan, Wilson and Austin to name the most common. These names house within itselfs those effects that can be reached at an operation of the present case. The operation methods may be divided into six main groups, namely the first only concerning soft part surgery, according to McBride, the second concerning proximal arthrodesis, i.e. arthrodesis with an angle alteration according to Lapidus, the third concerning proximal osteotomies, i.e. wedge-osteotomy, the fourth concerning mid-shaft osteotomies, for example scarf, the fifth concerns distal osteotomies, for example according to the names Reverdin, Mitchell, Wilson, Turan, Waterman, Youngswick and Austin and the sixth method concerning joint-cutting surgery, either a girdlestone according to Keller or arthrodesis. The methods most common, in superior, are within the fifth group and there the instrument according to the invention has its greatest benefit. The arthrodesis mentioned in method six may be apparently simplified by means of the instrument according to the present invention. The method described by Austin is based on so called chevron-osteotomy.

The description by Austin with chevron-methodology is automatically loadstable without internal fixation. It is with this method as a base the present invention has been developed. The instruments, on the market at present time, however, imply that only relatively simple, to the bone perpendicular or close to perpendicular osteotomies are carried out. At the slightest more difficult osteotomy it is a requirement of the operating orthopedist or surgeon to have a three dimensional eyesight and also an ability to correctly estimate angles. This is a quality missing in the main part of the population. Indeed extremely skilled carpenters may be able to estimate an angle but for ordinary people a mitre saw is required to be able to saw for example a door rail in an exact angle degree.

SUMMARY OF THE INVENTION

The aim of the present invention is to provide a new type of mitre instrument by means of which the drawback of the presently used instruments have been eliminated. The characterizing features of the invention are given in the following claims.

Thanks to the invention a mitre instrument is provided that in an emint way fulfils its aims at the same time as it is relatively simple and inexpensive to manufacture. By means of the instrument of the invention a displacement can take place at osteotomy towards any desired direction, towards or from the sole of the foot, shortening or extension, slanting towards any desired direction and also rotation. Just as in Austins description the use of the instrument of the invention mean that a load capacity is created directly after the operation and thus no internal fixation of the cut apart bones is needed. Thanks to the use of the instrument according to the invention a securing of the qualitative surgery results will be facilitated, which lead to less pain and shorter healingtime and additionally quicker return to work at the same time as risks are minimized for post operative complications due to the rapid mobilization.

The great advantages attained with the instrument according to the invention are, for example, obtaining a stable fixation at a simple hallux vulgus operation and this without using an internal fixation with screw or nail of the cut apart bones. The ends of the bones will namely lie fixed like the securing of a parquet flooring. This stability means in turn that the patient not only can, but shall, load the foot to 100% already about 1½ hour after the operation. The medium value for apparent post-operative pain is about 36 hours and this can be reduced by means of, in connection with the operation, giving long time effect anesthesia, which has effect 8-10 hours directly after the operation. In such a way the apparent pain period may be decreased to about 24 hours. The variation of the pain varies apparently, probably mostly due to respective personality of the patient. The majority of the patients cope to return to work within three days to a week after the operation. The groups of patients that need a longer period of sick-leave are, for example, firemen, buildingworkers and postmen.

The instrument or collection of instruments according to the present invention is actually formed of three mitre instruments where two of the instruments are constituted, above a basic embodiment, of a plus and a minus instrument, where the angles increase and decrease, respectively, with half a degree for each $15^{th}$ degree. With the help of this collection of instruments it is possible to secure that each orthopedist will be aided to saw in correct degrees. With the help of the collection of instruments it is thus possible to secure to attain an exact, predetermined angle at a new sawing in bone. The instruments are additionally fully balanced and the center of gravity is positioned in the middle of origin of coordinates. With a horizontally fixing pin in origin of coordinates the instrument will retain the position it is placed in. The plus and minus variants of the instrument make it possible to attain a stable and correct adaption of the cut bone ends. With the help of two of the three part instruments it is possible to practice long osteotomies, for example, even along nearly the whole metatarsal bone of the hallux. The large number of parallel holes in the instrument makes it possible to displace parallely the guide pins so they have the same direction.

BRIEF DESCRIPTION OF THE DRAWINGS

The invention is described in more detail below by means of a preferred example of an embodiment together with references to the appended drawings, in which.

DETAILED DESCRIPTION OF PREFERRED EMBODIMENTS

Figure 1:
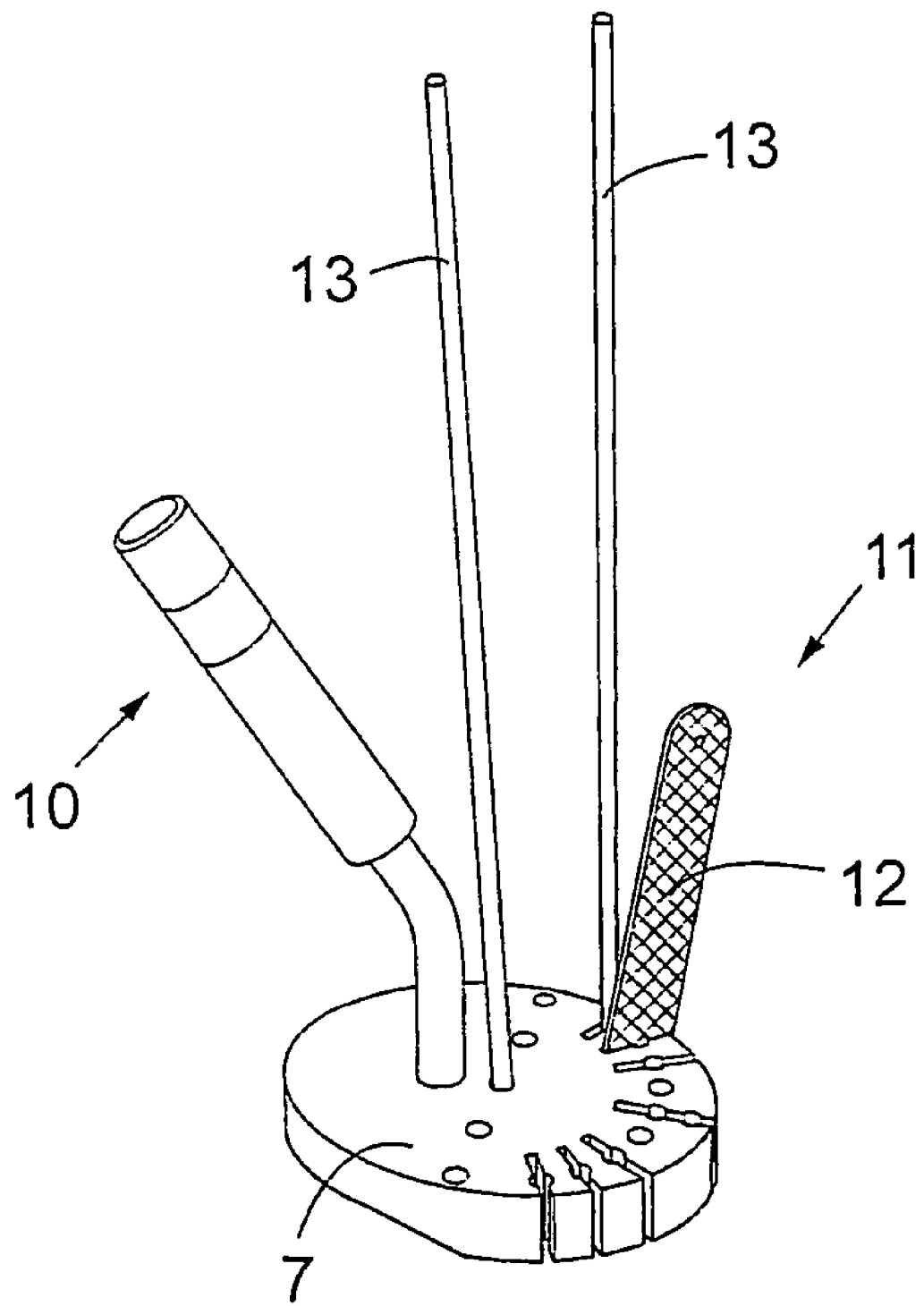
FIG. 1 shows a schematic perspective view of a basic embodiment of the instrument according to the invention.
Figure 2:
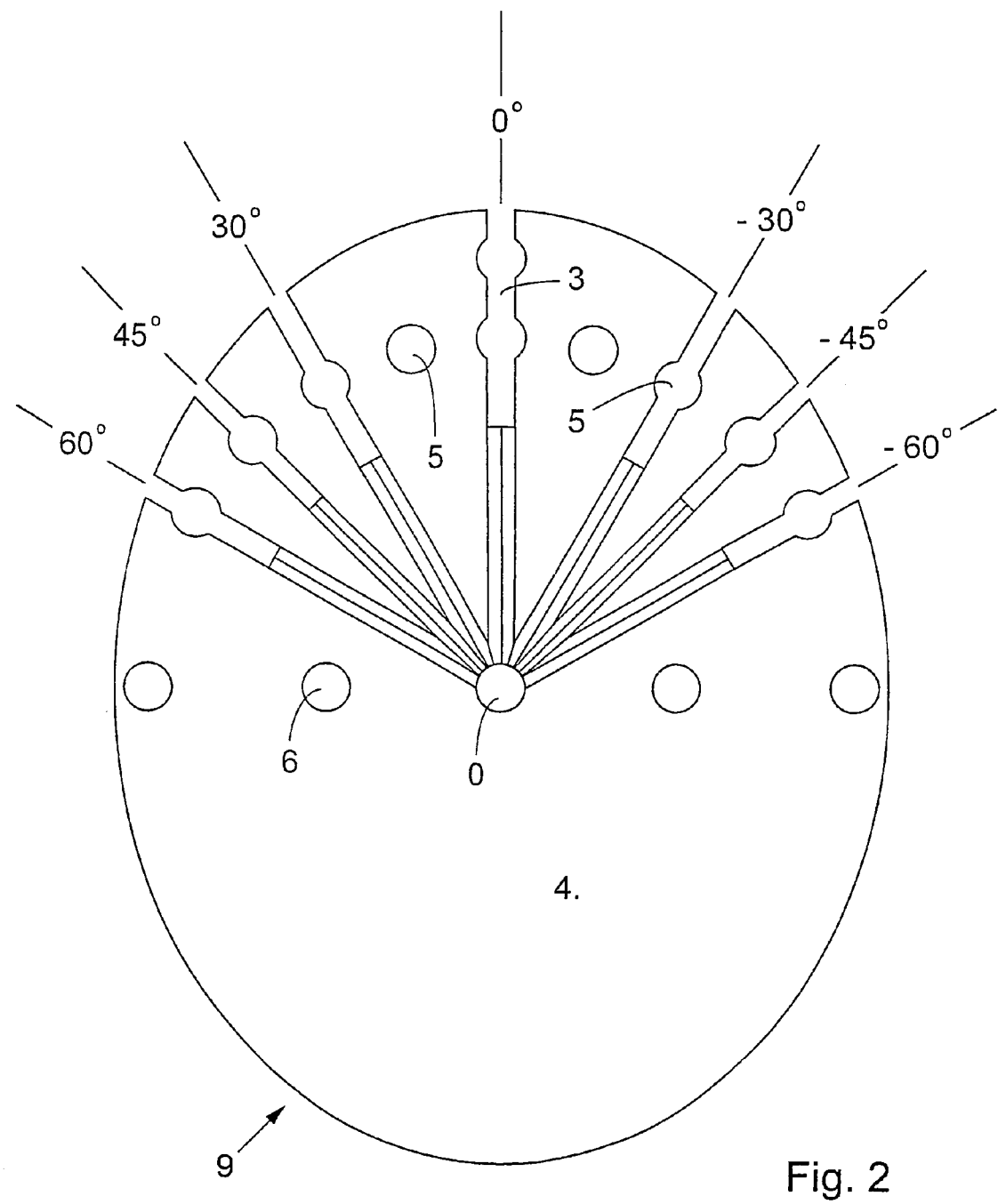
FIG. 2 shows a schematic plan view of the instrument seen from below, in which the slots for the cutting tool run into a common origin of coordinates, which is centrally positioned in a disc shaped body forming the instrument.
Figure 3:
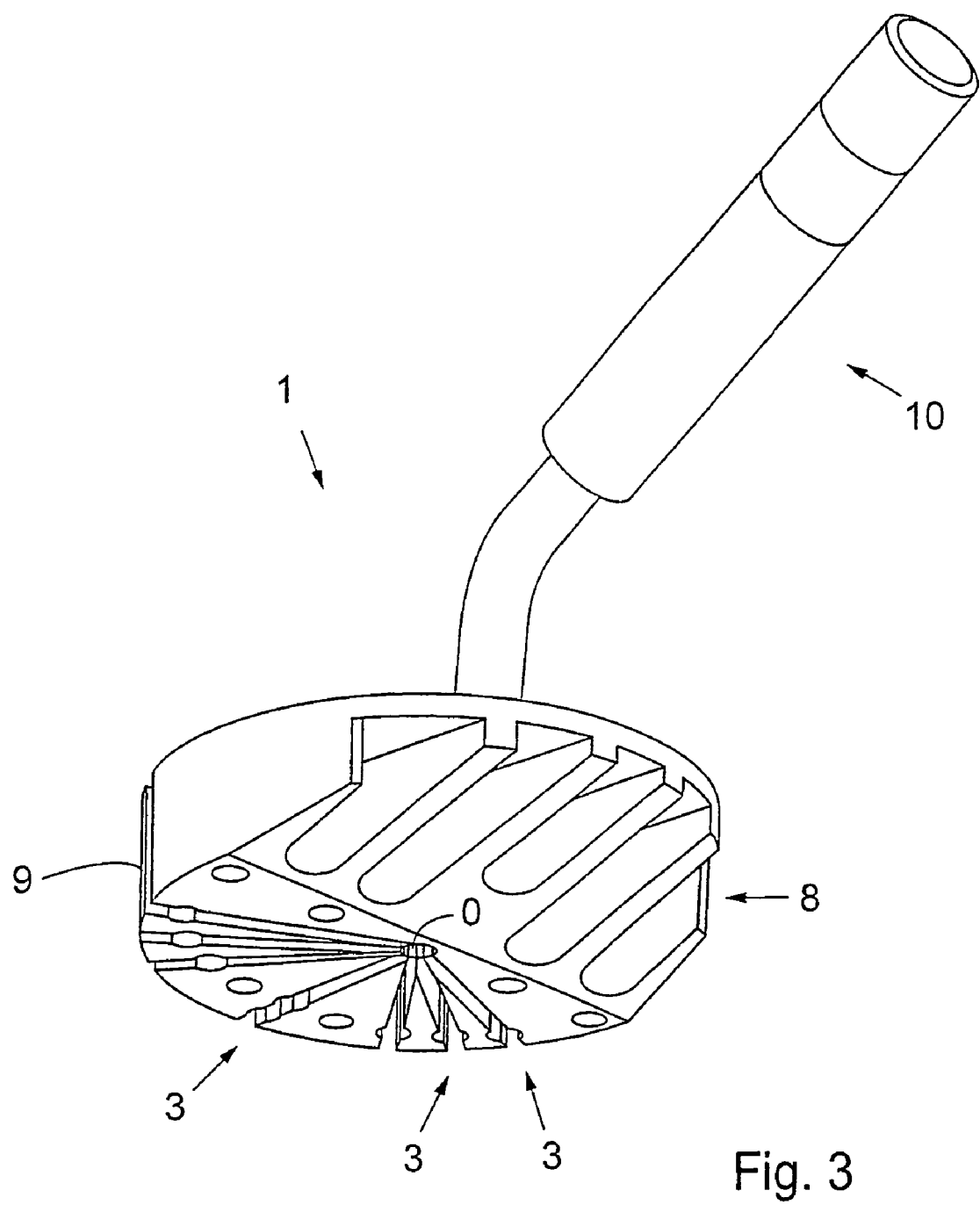
FIG. 3 shows a schematic perspective view obliquely from below of the instrument.
Figure 4:
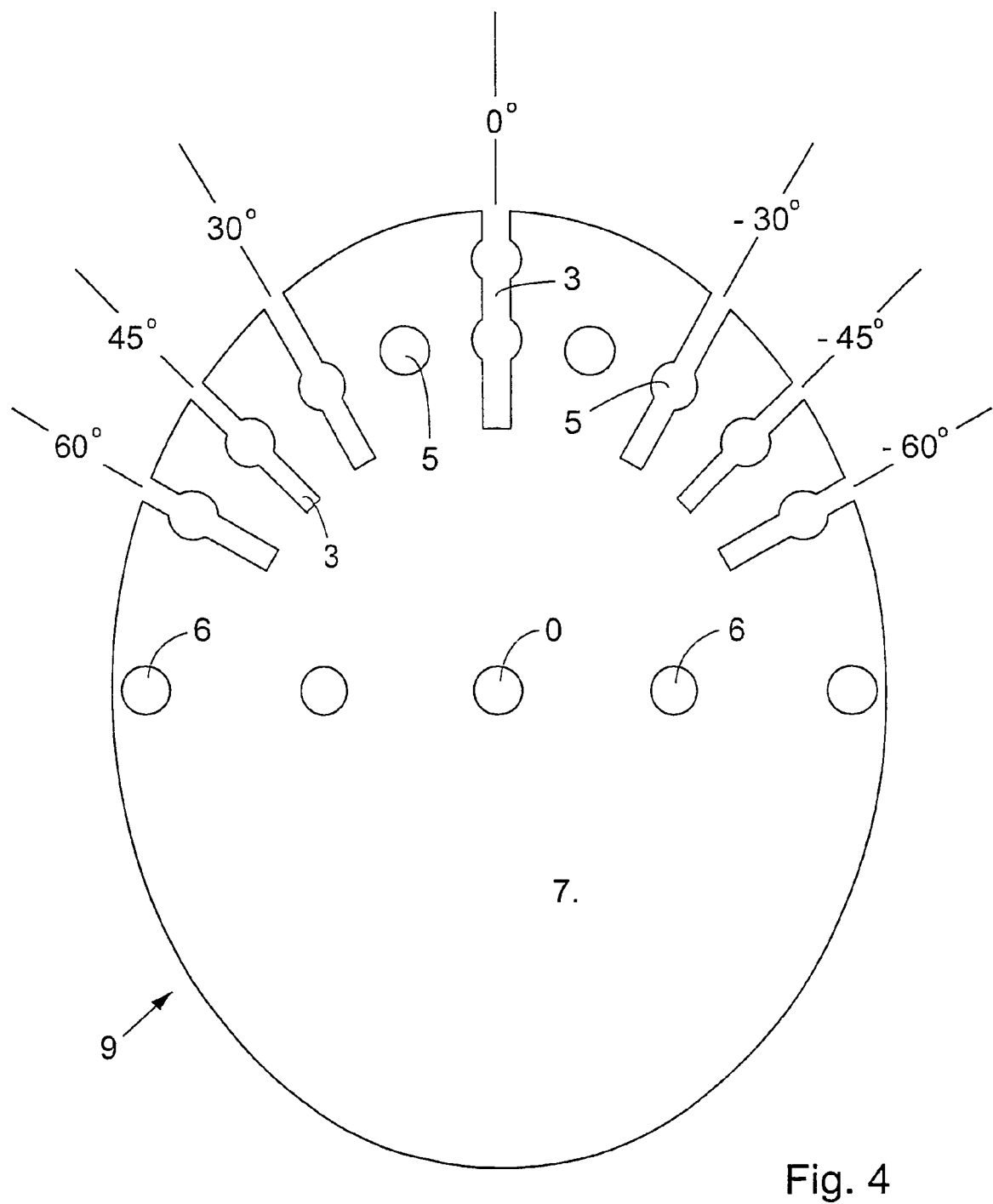
FIG. 4 shows a schematic plan view from above of the instrument and FIG. 5 shows a schematic perspective view obliquely from below of the instrument.
Figure 5:
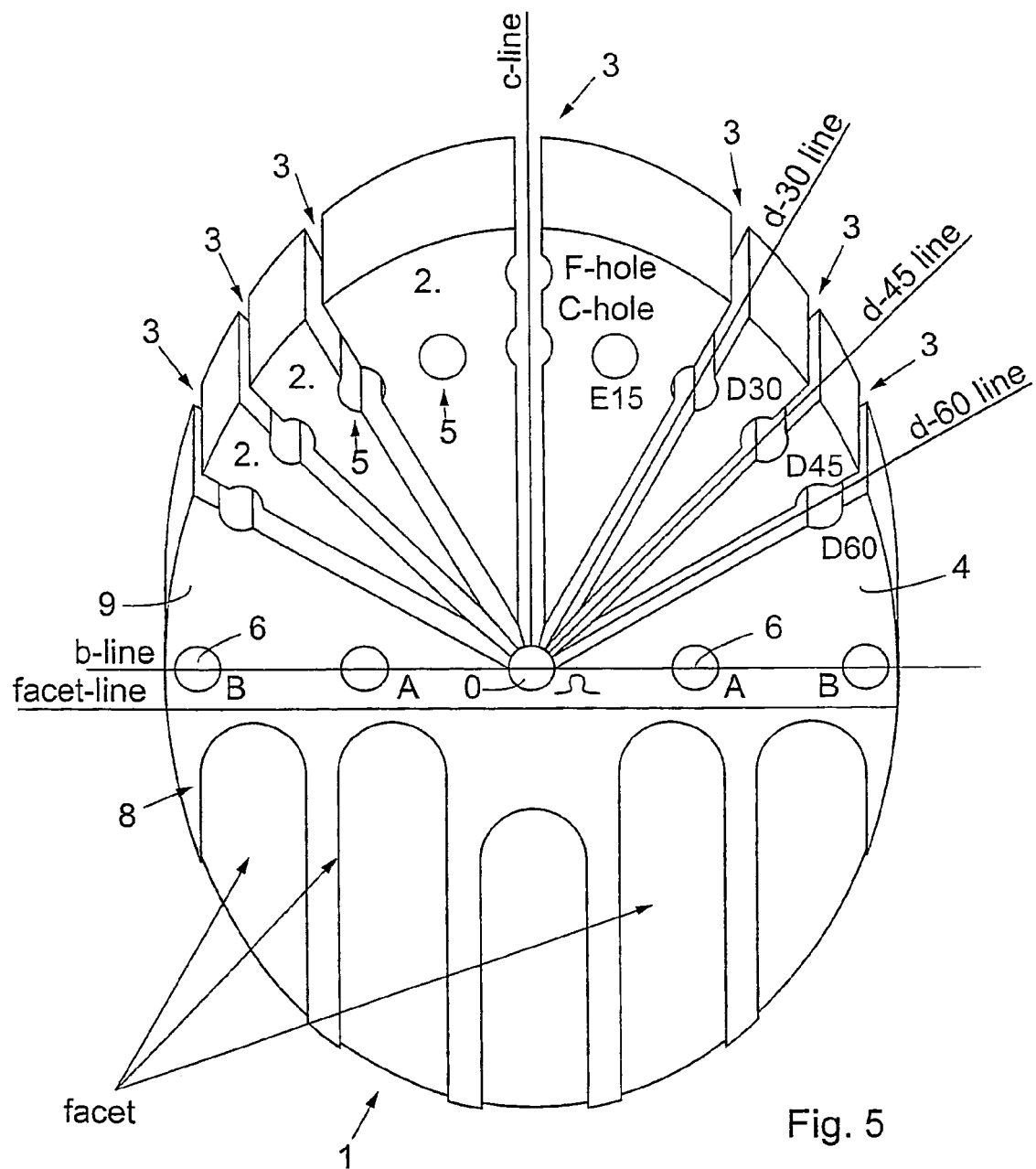

As emerges from the drawings the present invention comprises a mitre instrument 1 in its basic embodiment and to which there is a plus and a minus instrument, where the angles increases and decreases, respectively, with half a degree for each $15^{th}$ degree. The basis for the instrument 1 according to the invention is constituted briefly of the fact that it comprises fixed angles, which converge in a central, in the instrument positioned, common origin of coordinates 0 and that without so called "pieces of cake" 2 positioned therebetween falling off. The instrument further comprises slots or scores 3, which extend obliquely downwards in the instrument in such a way that a cutting tool 11, such as a saw blade 12, which is for cutting the bone in question may reach out at an outlet of a guide pin 13 in origin of the coordinates 0 on the lower side 4 of the instrument 1 and this is the fact that makes the possibility for these slots 3 to be present without the pieces of cake 2, falling off. A further basis for the invention is that the instrument also is formed, above its base embodiment, with a plus and a minus variant, which means that the small differences in angle between the neutral instrument and the plus or minus instrument lead to that a stability in the bone to be cut is attained. The mitre instrument comprises fixed distances from the centre, i.e. origin 0, for holes 5 in the same, which are provided for the fixation of the instrument. The instrument has also prepared holes 6 for adaption of specially construed Hohman hooks.

The lower side 4 of the instrument 1 which in the shown example is grooved, shows a beveling or beveled edge 8, which extends across about half of the lower side 4. The inclination of the so called "facet" is about 20-22°, which design facilitate the estimation of angle at the most common, i.e. shortening, effect of osteotomy. The collection of instruments according to the invention may also be used for hand surgery and then in a reduced size and for correction osteotomies on lower legbones and thighbones.

The mitre instrument according to the invention comprises, as evident from the drawing and especially FIG. 1, an elliptic, disc shaped body 9, which may have a thickness of about 7 mm with ellipse diameters of 22×28 mm. The instrument comprises thus as mentioned above in its entirety of three to each other complementing parts and besides a so called neutral variant there are a plus and a minus variant with some what differing degrees between the slots 3 made in the disc shaped bodies 9.

On the instrument, i.e. all variants, there is a gripfriendly handle formation 10 with ergonomically optimal angle and length. The handle formation 10 is additionally an assistance when balancing the three instrument variants. In the elliptic disc shaped body 9, which forms the instrument according to the invention, there is as is evident from the drawings a number of holes 5, 6 for guide or fixation pins 13 and slots or scores 3 for a cutting tool 11. The holes 5 are positioned in the angles +15°, −15°, +30°, −30°, +45°, −45°, +60°, −60°. In the same angles as above there is also slots 3 for the saw blade 12 of the cutting tool 11. The slots 3 have an inclination within the goods from the upper side 7 of the instrument 1 towards its lower side 4 of about 45° so that an oscillating saw easily can be handled. On the lower side 4 there is a "facet" 8, which has an inclination of about 20-22°. For correction of the centre of gravity of the instrument the "facet" 8 may be grooved.

The plus and minus variants of the instrument have the same design as the neutral variant with the difference that the angles have been displaced so that they increase (plus variant) and decrease (minus variant), respectively with half a degree for each $15^{th}$ degree.

The technical advantages with the collection of instruments according to the invention is namely that the fixed angles, which are built into the instruments, bring about the full security that the angle chosen corresponds to the angle aiming at when cutting during an operation. At osteotomy with double chevrons, i.e. double angle cuts and removal of bone, one can be sure that the resection surfaces in the bone will exactly fit each other again after the cutting. This exactness in cutting lead to secure the results of the operations and shortening of the convalescence after the operation. The collection of instruments according to the invention lead to a security to operations performed by less experienced surgeons and the collection of instruments also lead to that pins for fixing of the mitre instruments can be displaced parallely with great exactness. Finally the collection of instruments according to the invention are fully balanced and do not rotate out of its position due to gravity, like corresponding previously known instruments that have been used up till now in this type of operations.

The invention claimed is:

1. A mitre instrument for use during surgery when cutting bone in connection with shortening or extension and/or correcting of the angle of the bone, comprising: a body including an upper surface, a lower surface, an edge forming an outer periphery of said body, a common opening located substantially near a center of said body, at least one hole for a guide pin for fixation of the instrument, and at least two slots or scores extending from said edge toward said common opening for receiving a cutting tool, wherein on said lower surface of said body, each of said slots begins at said common opening and angularly extends from said common opening to said edge of said body so as to form wedge-shaped portions of said body between said slots, and wherein on said upper surface, each of said slots extends from said edge of said body to a point located a spaced distance from said common opening such that each of said slots connects said lower surface to said upper surface of said body at said edge but does not connect said lower surface to said upper surface in an area between said common opening and said point located a spaced distance from said common opening.

2. A mitre instrument according to claim 1, wherein said at least one hole for the guide pin is provided a fixed distances from said common opening.

3. A mitre instrument according to claim 1, wherein said slots angularly extend from said common opening with a positive displacement from each other of +0.50° each $15^{th}$ degree, with a negative displacement of −0.5° each $15^{th}$ degree or without the displacements.

4. A mitre instrument according to claim 1, said lower surface of said body has a bevel in the form of a facet, which forms an inclination of about 20° relative to said lower surface.

5. A mitre instrument according to claim 4, further comprising an angled handle formation attached to said upper surface of said body near an area above said common opening and mainly in an area close above the inclination of said facet away from said lower surface of said body.

6. A mitre instrument according to claim 5, wherein said handle formation is suitable for gripping, is positioned at an ergonomically optimal angle, and has a length that allows the instrument to be balanced.

7. A mitre instrument according to claim 4, wherein said facet includes a grooved lower side.

8. A mitre instrument according to claim 1, wherein each of said slots has an inclination within said body from said upper surface toward said lower side of about 45° for facilitating handling of the cutting tool.

9. A mitre instrument according to claim 1, wherein the instrument is balanced so that a point of gravity of the instrument is positioned in said common opening.

10. A mitre instrument according to claim 1, further comprising a plurality of holes for guide pins, said holes arranged parallel relative to each other for a possibility of parallel displacement of the guide pins.

* * * * *